United States Patent [19]
Phelps et al.*

[11] Patent Number: 5,522,822
[45] Date of Patent: *Jun. 4, 1996

[54] VASOOCCLUSION COIL WITH ATTACHED TUBULAR WOVEN OR BRAIDED FIBROUS COVERING

[75] Inventors: James J. Phelps, Sunnyvale; Nga T. Van, Santa Clara, both of Calif.

[73] Assignee: Target Therapeutics, Inc., Fremont, Calif.

[*] Notice: The term of this patent shall not extend beyond the expiration date of Pat. No. 5,382,259.

[21] Appl. No.: 323,951

[22] Filed: Oct. 17, 1994

Related U.S. Application Data

[63] Continuation of Ser. No. 956,973, Oct. 26, 1992, Pat. No. 5,382,259.

[51] Int. Cl.⁶ .................................................. A61B 17/00
[52] U.S. Cl. ........................................ 606/151; 606/191
[58] Field of Search ........................... 606/108, 151, 606/191, 198, 194; 604/104, 105, 107; 623/1, 12

[56] References Cited

U.S. PATENT DOCUMENTS

| | | |
|---|---|---|
| 3,687,129 | 8/1972 | Nuwayser . |
| 3,834,394 | 9/1974 | Hunter et al. . |
| 4,754,685 | 7/1988 | Kite et al. . |
| 4,870,887 | 10/1989 | Tresslar et al. . |
| 4,921,484 | 5/1990 | Hillstead . |
| 4,994,069 | 2/1991 | Ritchart et al. . |
| 5,064,435 | 11/1991 | Porter . |
| 5,078,726 | 1/1992 | Kreamer . |
| 5,108,407 | 4/1992 | Geremia et al. . |
| 5,151,105 | 9/1992 | Kwan-Gett . |
| 5,211,658 | 5/1993 | Clouse . |
| 5,226,911 | 7/1993 | Chee et al. ............... 606/191 |
| 5,354,295 | 10/1994 | Guglielmi et al. ......... 606/191 |
| 5,382,259 | 1/1995 | Phelps et al. ............. 606/151 |

FOREIGN PATENT DOCUMENTS

| | | |
|---|---|---|
| 0385925 | 9/1990 | European Pat. Off. . |
| 0464755 | 1/1992 | European Pat. Off. . |
| 2671482 | 7/1992 | France . |

*Primary Examiner*—Tamara L. Graysay
*Attorney, Agent, or Firm*—Morrison & Foerster

[57] ABSTRACT

This invention is in the field of vasoocclusion devices. More particularly, it relates to a vasoocclusion coil which may be segmented, onto which a fibrous, woven or braided, tubular covering or element is attached.

17 Claims, 11 Drawing Sheets

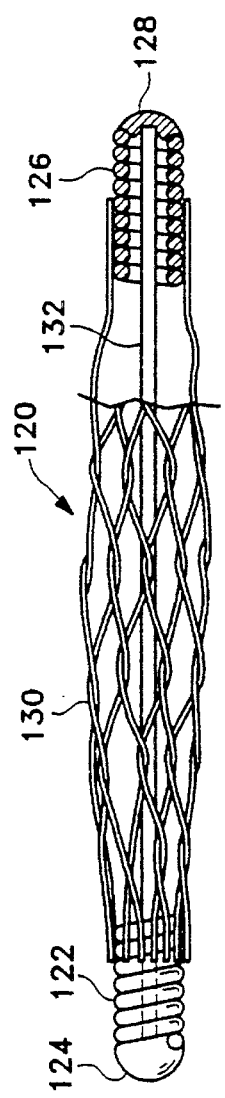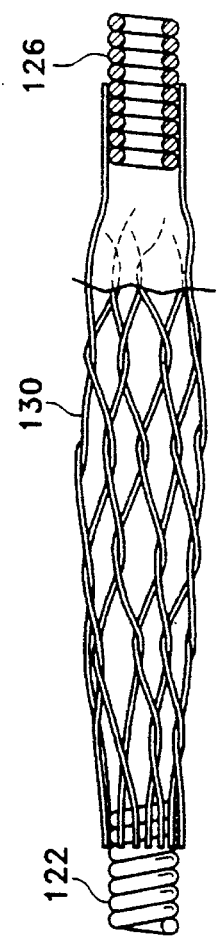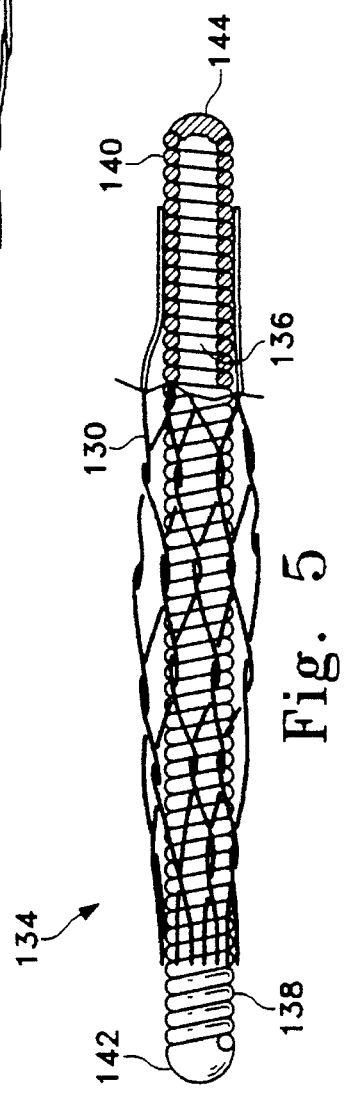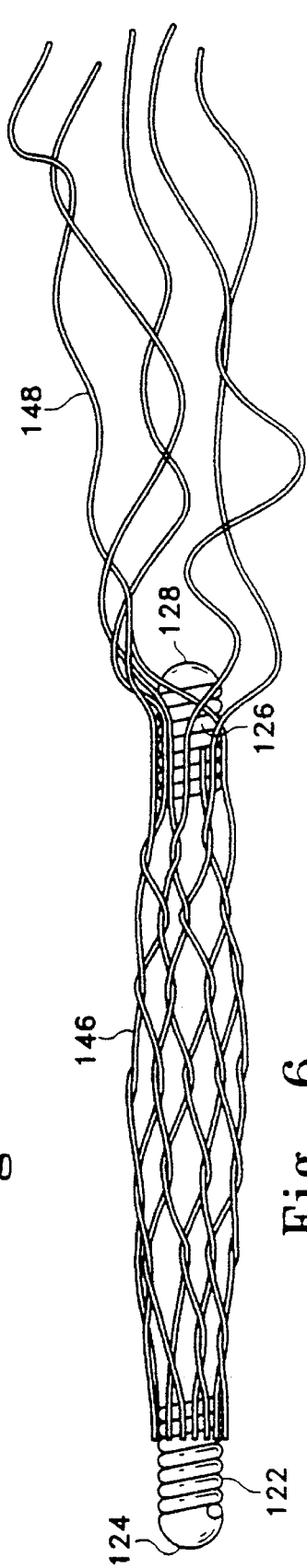
Fig. 4
Fig. 7
Fig. 5
Fig. 6

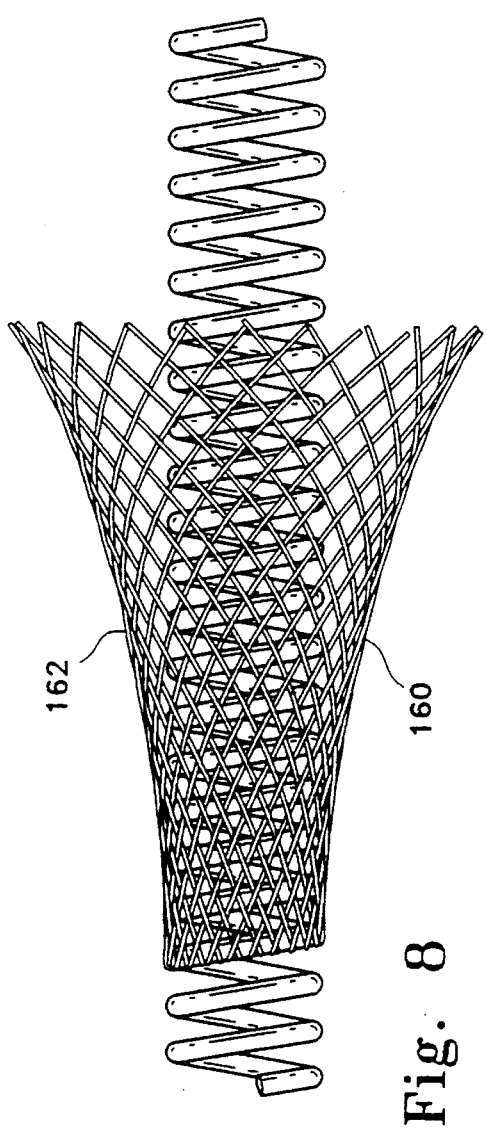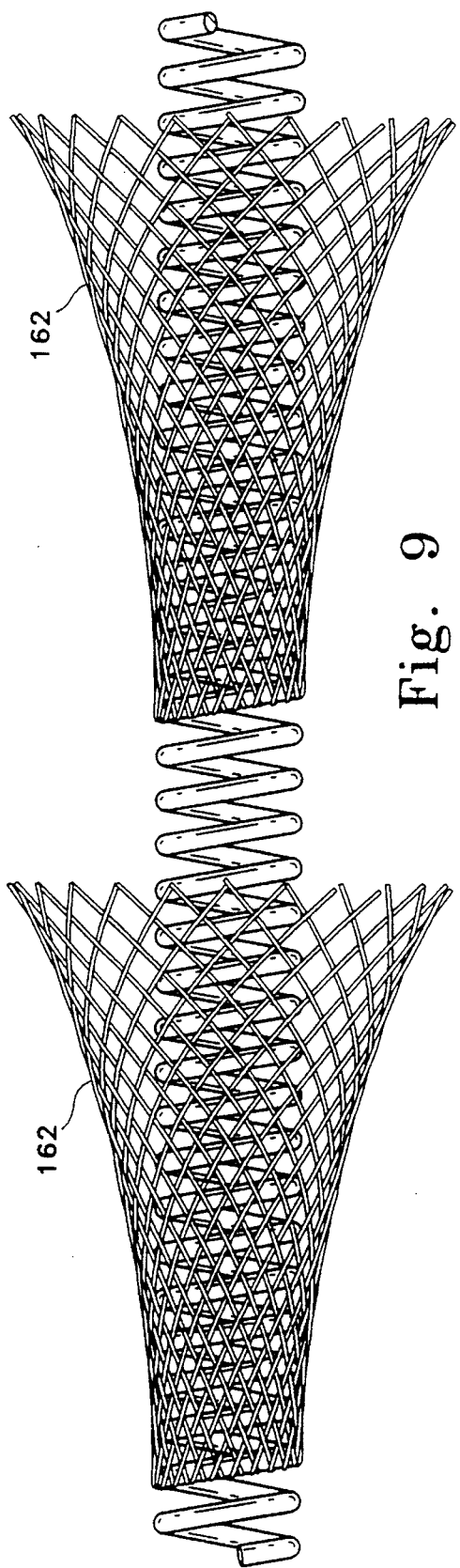

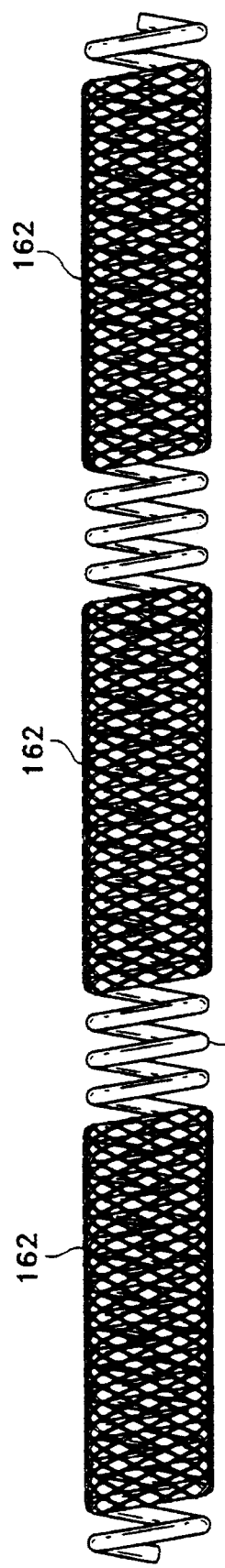
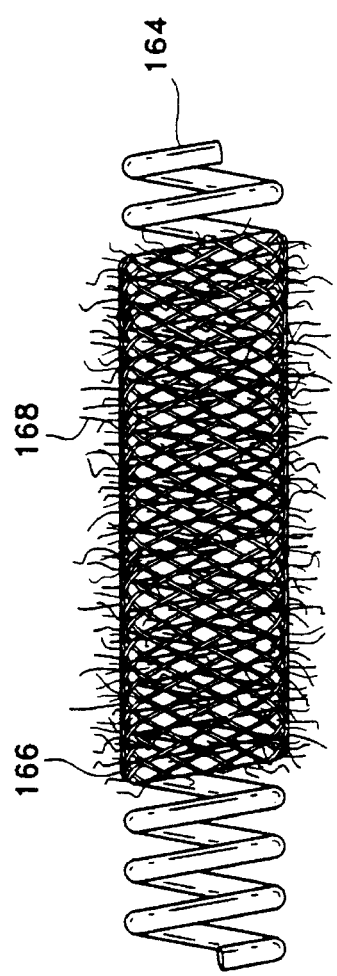
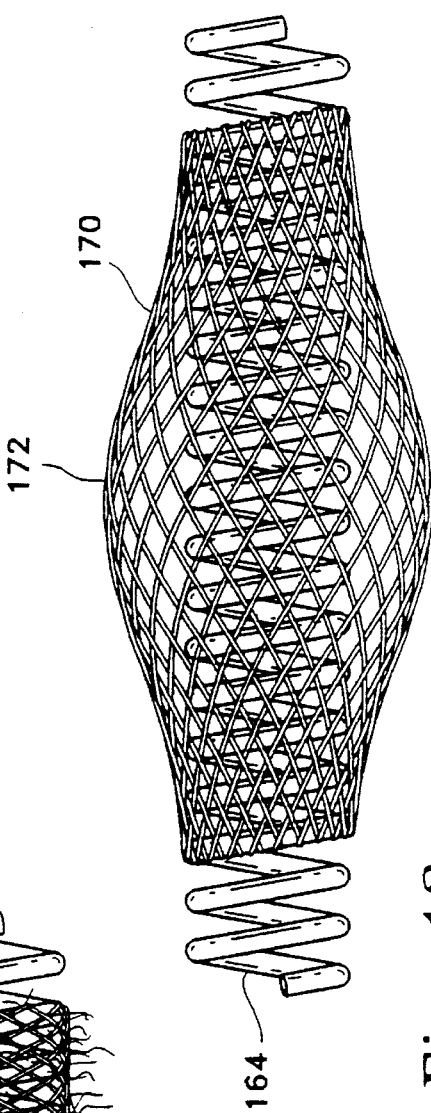
Fig. 10
Fig. 11
Fig. 12

VASOOCCLUSION COIL WITH ATTACHED TUBULAR WOVEN OR BRAIDED FIBROUS COVERING

This application is a continuation, of application Ser. No. 07/965,973 filed Oct. 26, 1992 now U.S. Pat. No. 5,332,259.

FIELD OF THE INVENTION

This invention is in the field of vasoocclusion devices. More particularly, it relates to a vasoocclusion coil which may be continuous or segmented, onto which a fibrous, woven or braided, tubular covering or element is attached.

BACKGROUND OF THE INVENTION

Vasoocclusion devices are surgical implements that are placed within the vasculature of the human body, typically via a catheter, to block the flow of blood through the vessel making up that portion of the vasculature or within an aneurysm stemming from the vessel. One widely used vasoocclusive device is a helical wire coil having windings that are dimensioned to engage the walls of the vessels. Fibers may also be woven or laid crosswise through the windings to provide a substrate for clot formation and tissues growth within the chosen site. Coils having such a structure are readily commercially available.

U.S. Pat. No. 4,994,069, to Richart et al., describes a vasoocclusive coil which assumes a linear helical configuration when stretched, and a folded convoluted configuration when relaxed. The coil is introduced into the human body in a stretched condition. When the coil reaches its intended site, the coil assumes its relaxed condition—which is better suited to occlude the vessel—and restricts blood flow beyond the space that it occupies.

U.S. patent application Ser. No. 07/771,013, to Chee et al., teaches a helical vasoocclusion coil to which fibrous elements are attached in such a way that they will not be dislodged from the coil. The fibrous elements enhance the ability of the coil to fill space within the vasculature and to facilitate clot formation and tissue growth.

Care must be taken in creating combination fibrous coils, i.e., those containing metal coils and fibrous elements, since the fibrous elements may come off and move to vessels supplying blood to normal tissue. Fibrous elements, since they are not normally radiopaque, are difficult to find and to retrieve if separated from the metallic coil. Nevertheless, it is desireable to increase the ratio of fibrous element to the metallic coil since the fibrous element increases the tendency at the coil assembly to cause embolic and tissue growth.

The inventive coil assembly is desireable in that the ratio of fibrous material to metallic material is quite high, the fibrous material is held firmly in place due to the braided or woven configuration, and is easily placed within the body's vasculature.

SUMMARY OF THE INVENTION

This invention is a vasoocclusive device comprising:
(a) a helical coil which may be segmented, continuous, or segmented having a gap between the two end portions, but in each case having a first end and a second end;
(b) at least one fibrous woven or braided tubular element or covering attached to the exterior of the helical coil.

BRIEF DESCRIPTION OF THE DRAWINGS

FIGS. 2–21 are side views or partial cross-sectional side views of a number of embodiments of the inventive vasoocclusive device.

DESCRIPTION OF THE INVENTION

Figure 1:
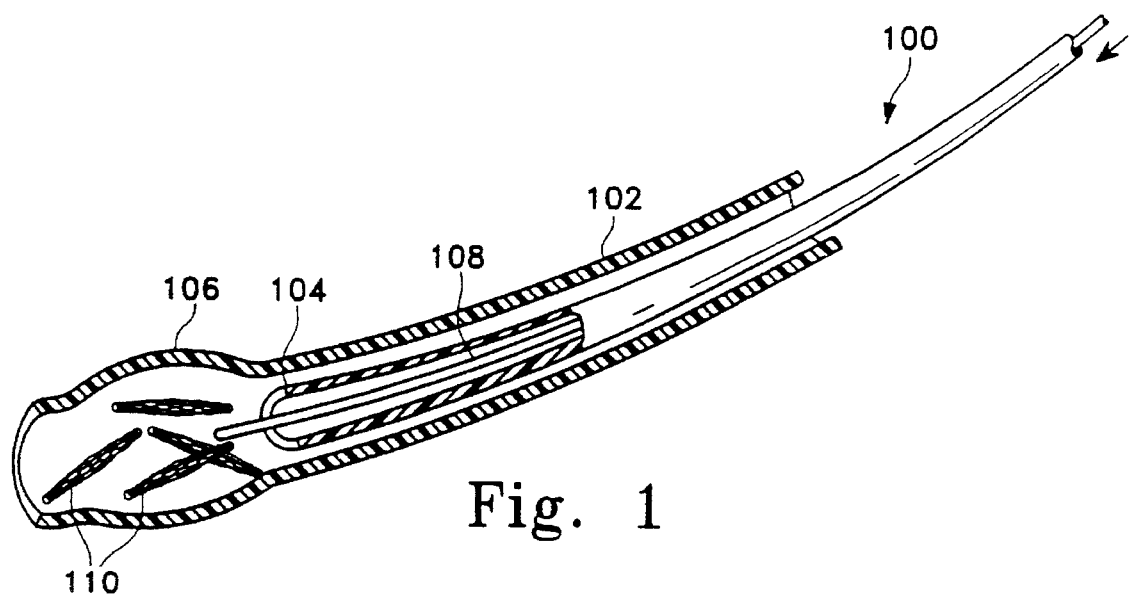
FIG. 1 is a schematic depiction of an overall system for introducing the inventive devices into the vessel of a human body.

The vasoocclusive devices of this invention may be used in a manner similar to those described in U.S. Pat. No. 4,994,069. Briefly, the coil devices may be supplied in a prepackaged form in a sterile cannula which is adapted to engage the proximal end of a catheter. As is shown in FIG. 1, once the catheter (100) is in place within a vessel (102)—for instance, the distal end (104) of the catheter (100) at an aneurysm (106)—the coil-containing cannula is placed into engagement with the proximal end of the catheter and the coils are transferred from the cannula lumen into the catheter lumen by exerting force on the proximal end of the coil. A flexible pusher device (108) is used to push the coil (110) through the catheter (100) to the desired coil release site. The location of the coils (110) may be observed due to the radial opacity of the metallic coils. Once at the site, the coils are singularly plunged from the catheter lumen into the vessel site (106).

Figure 2:
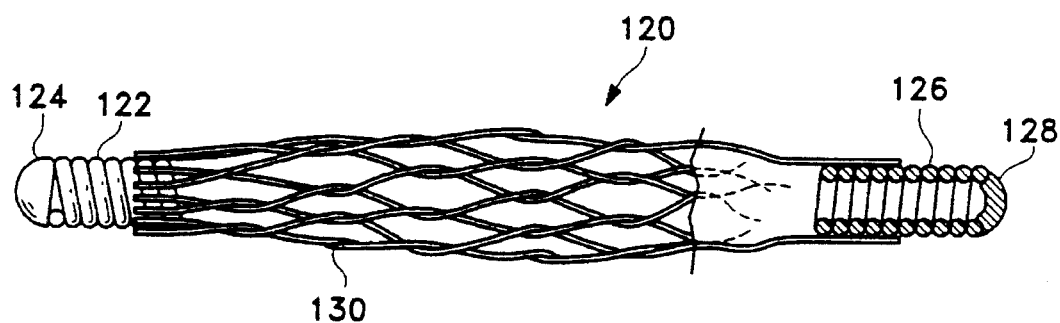

FIG. 2 depicts one embodiment of the vasoocclusive coil of the invention, generally shown as (120). The vasoocclusive device (120) has several components: a first helical coil end (122), a cap (124), a second helical coil end (126), a cap (128), and a braided or woven tubular fibrous element extending from near the termination of the first helical coil (122) and to a similar position on the second coil end (126). In this variation, the coil is segmented and has a gap beneath the fibrous tubular element (130).

Coil ends (122) and (126), variously in this configuration and in the others discussed herein, will typically be made of a radiopaque material such as platinum, tungsten, gold, silver, or alloys thereof, or other suitable generally radiopaque metals which are otherwise biologically inert. The diameter of the wire will typically be in the range of 0.0005 and 0.005 inches. The resulting primary coil diameter will normally be 0.008 to 0.018 inches. Preferably, the coil primary diameter is 0.015 to 0.018 inches. Preferred is a platinum-tungsten alloy forming a coil having a diameter of 0.015 to 0.018 inches. The axial length of the coil will usually be in the range of 0.5–100 cm., more usually 2.5 to 40 cm. The coil will typically have 10–71 windings per cm, more typically about 10–40 windings per cm, the coil windings may be regular. The fibrous woven or braided tubular member (130) may be made from a biocompatible materials such as Dacron (polyester), polyglycolic acid, polylactic acid, fluoropolymers (polytetrafluoroethylene), nylon (polyamide), or silk. The strands forming the braid should be reasonably heavy, e.g., having tensile strength of greater than about 0.15 pounds. The materials mentioned, to the extent that they are thermoplastics, may be melted or fused to the coils. Alternatively, they may be glued or otherwise fastened to the coils. Preferred materials are Dacron strands using the process of fusing to attach the strands to the coil surface.

The caps (124) and (128) shown in FIG. 1 may be independently applied materials such as glues or biocompatible solders, but typically are formed merely by melting the tips of the coils or the braided polymer. The fibrous elements may be a bundle of individual fibers, e.g., between 5 and 100 fibers per fibrous bundle, preferably 20 to 30 fibers per bundle, or may be monofilaments.

Figure 3:
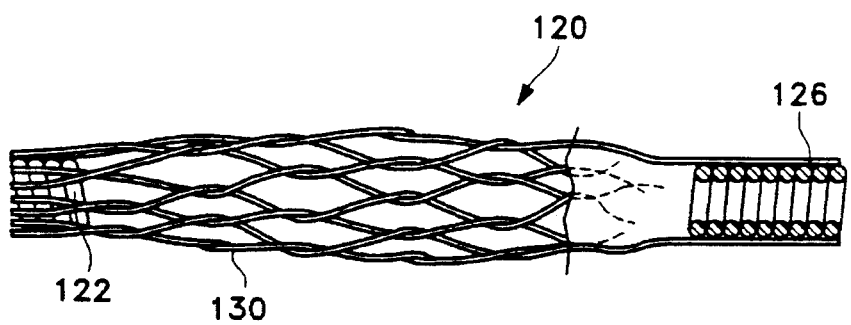

FIG. 3 shows another variation of the inventive vasoocclusive device (120). In this variation, may be found first coil (122) and second coil (126). The tubular braid (130) in this variation extends all the way to the end of the respective coil ends. In addition to the braid extending to and being fixedly attached to the end coils (122) and (126), the device lacks end caps. In this way, the vasoocclusive device may be strung on a catheter guide wire (similar in operation to that wire or rod 108 shown in FIG. 1) and may be pushed off the end of the wire using a coaxial sleeve.

FIG. 4 shows a further variation of the inventive device (120) in which the braid (130) extends from near the ends of the respective coil ends (122) and 126. In this variation, wire (132) is placed between the end caps (124) and (128). The wire (132) may be wound in any configuration including straight coils or C-shaped coils or the like. The wire (132) is typically made of stainless steel but may be made of other appropriate materials including shape memory alloys such as Nitinol. Nitinol wire having the proper transition temperature allows the device to be introduced through the catheter in a linear fashion and upon raising the temperature of the vasoocclusive coil to body temperature, the wire assumes its pre-selected shape.

FIG. 5 shows another variation of the inventive vasoocclusive device (134). In this variation the coil (136) is not segmented but is continuous from a first end (138) to a second end (140). First end cap (142) is found on the first end of the coil and a second cap (144) is found on the second end. The braided or woven tubular element (130) is found on the outside of the coil (136) and runs substantially from the first end (138) of the coil (136) to the second end (140). Coil (136) may be given a specific shape prior to its introduction into the catheter. For instance, the coil may be pre-shaped to form a "C" when ejected from the tip of the catheter lumen. During its traverse through the lumen, it would be constrained by the catheter or maintain a linear shape. Caps (142) and (144) may be omitted from this design as desired.

FIG. 6 shows another variation of the inventive vasoocclusive coil having a first coil end (122) with a first cap (124) second coil end (126) with a cap (128). This device obviously has a segmented coil portion. The braided or woven tubular covering (146) extends from near the tip of the first coil end (122) to the second cap (128). In addition, the tubular member has tassels (148) which extend past the end of the coil. This feature provides additional occlusion area and adds very little to the volume of the device as it passes through the catheter lumen.

FIG. 7 shows a vasoocclusive device very similar in design to the FIG. 3 device. It differs in that the braided covering does not extend to the ends of first coil end (122) nor second coil end (126). As is apparent from FIG. 7, the coil is a two-piece segment with a gap between the two segments.

FIG. 8 shows a vasoocclusive device in which the braid 160 is loosely woven and is attached only at one end 162 of the braid. FIG. 9 shows a similar device in which multiple fibrous braids 162 are attached to a single coil.

FIG. 10 shows a variation of the vasoocclusive device in which a number of independent braided sections 162 are included on a single continuous coil 164. The braid is attached to the coil at multiple locations in this variation.

FIG. 11 shows a device in which a fibrous element overlies the coil 164. The fibrous braided portion is constructed to have exposed fiber elements 168 sticking out from the fiber tubular member. This variation enhances the ability of the device to effectively fill the space at the target within patient's vasculature.

FIG. 12 shows a device in which the fibrous outerlying element 170 is axially compressed prior to installation upon the coil so that it bulges from the middle of the coil. This bulging 172 allows the combination to occupy more space once it is placed within the patient's vasculature.

FIGS. 13 through 19 show a variety of complex coil shapes covered with a braided or woven covering. The coil cores in these variations are found, e.g., in U.S. Pat. No. 4,994,069 mentioned above. These coil typically only assume their convoluted configurations upon ejection from the catheter tip.

Figure 13:
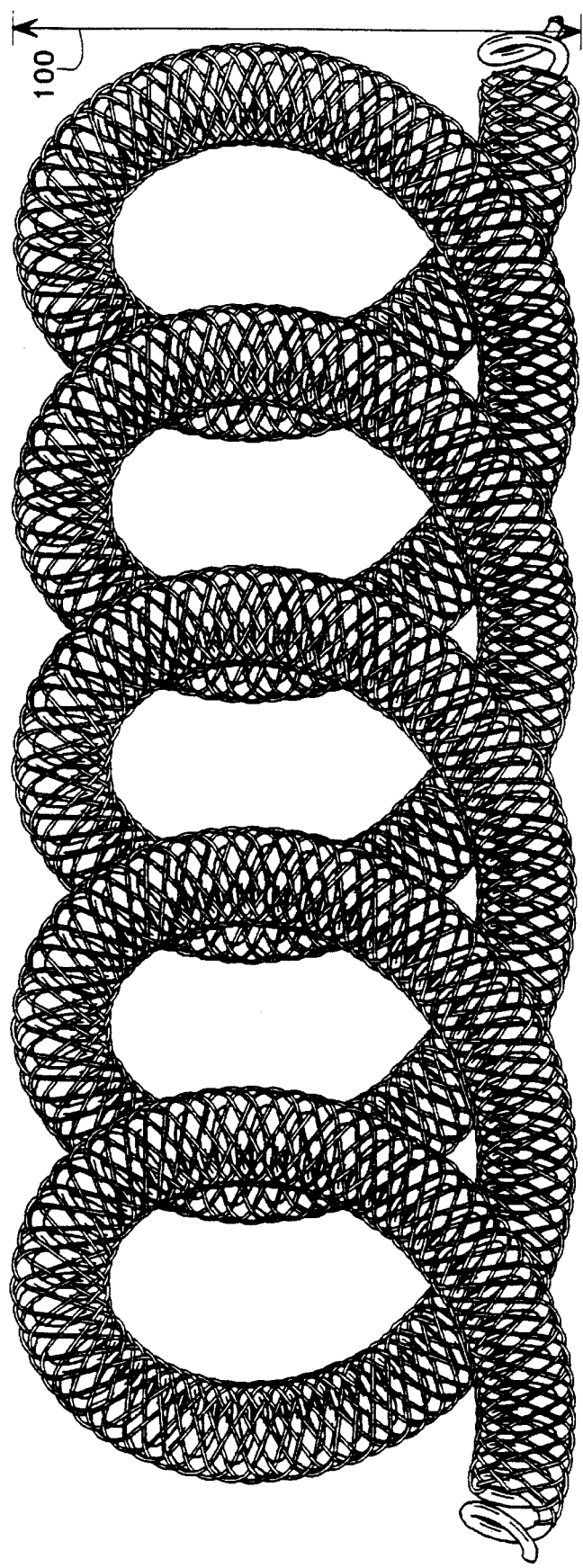
Figure 14:
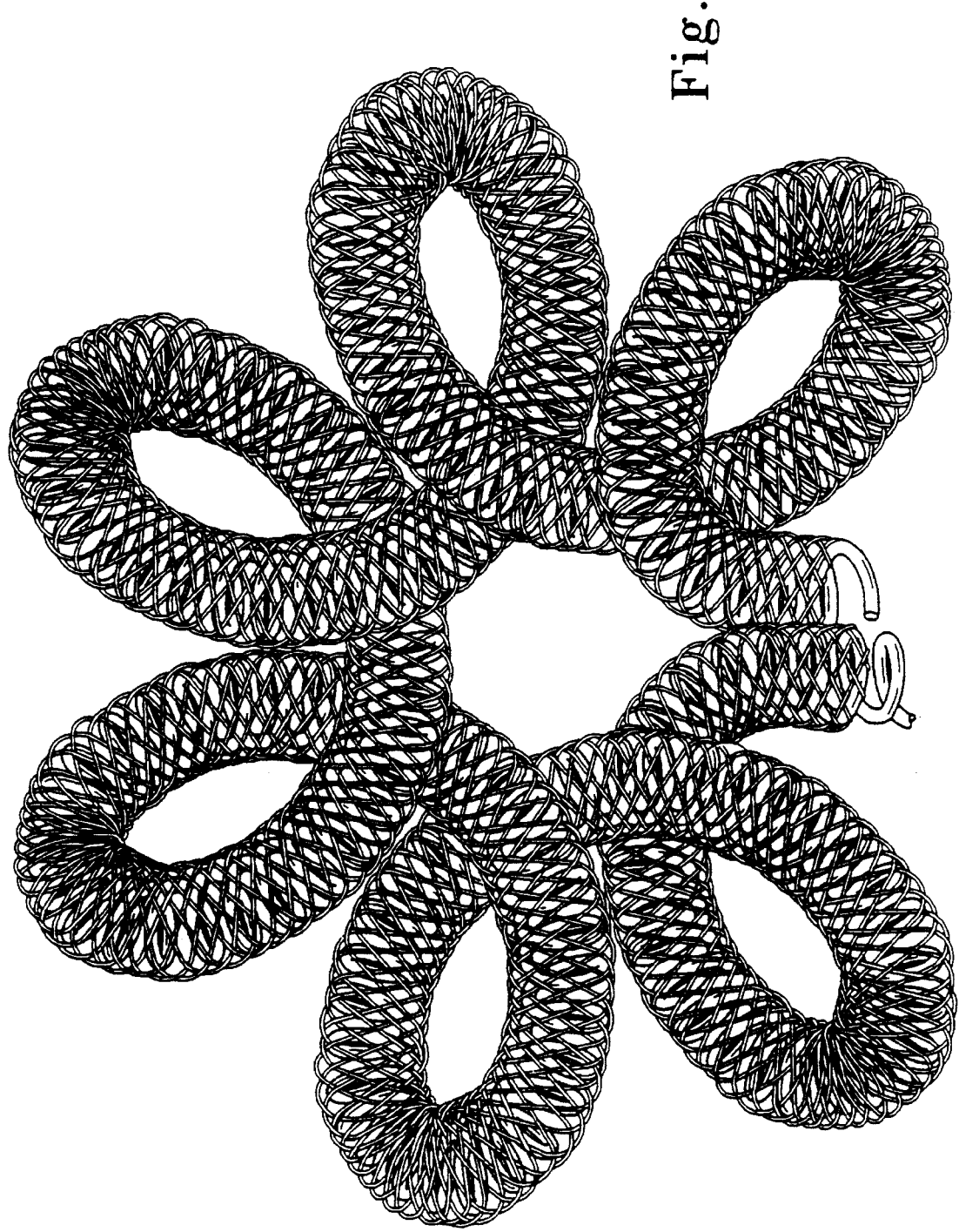

FIG. 13 shows a simple multi-loop coil 174 having a small primary diameter but a large secondary diameter 176 (150). The secondary diameter (150) is often chosen to match that of the inside diameter of the vascular site. The presence of the braided material on the outside of the coil helps to occlude that site. Similarly, FIG. 14 shows a coil 178 having a configuration as that of FIG. 13 except that it is given an added amount of twist to allow assumption of a large symmetrical flower-like design upon its relaxation after leaving the tip of the catheter. This configuration, with its braided cover 180, permits filling of a large vascular space with a coil and which filling is enhanced by the braided or woven covering.

Figure 15:
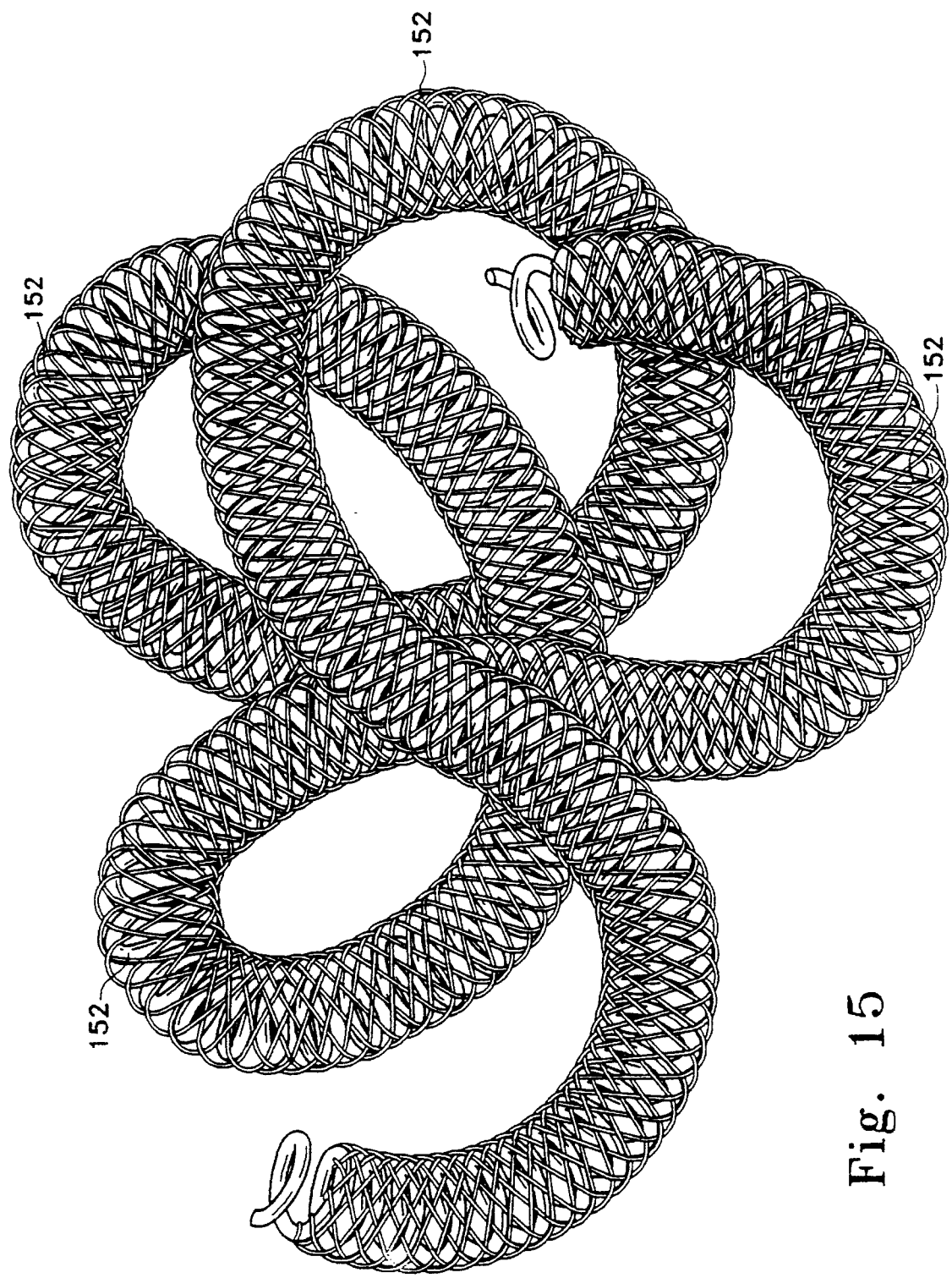

FIG. 15 shows still a further variation of the invention. In this variation, the coil 182 has been precrimped 152 so to precondition the coil to form a random configuration upon its relaxation. Again, the braided or woven covering 184 enhances the ability of this random coil to occlude the site at which it is placed.

Figure 16:
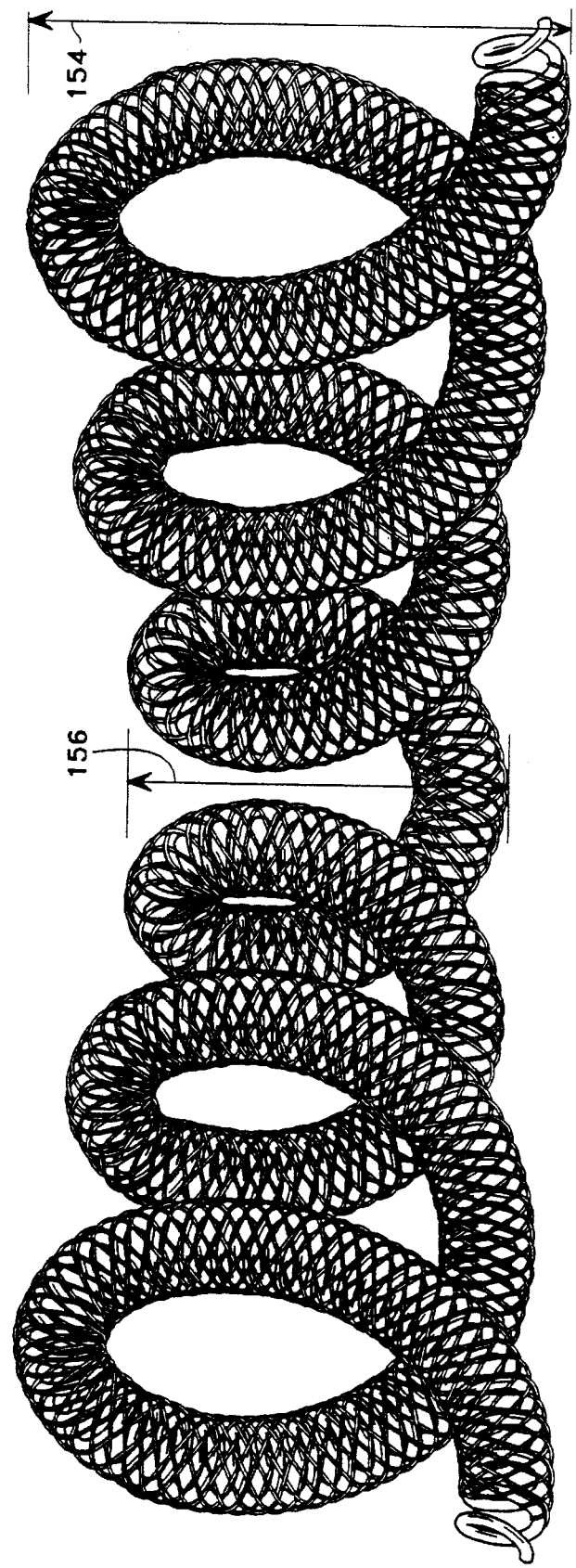

FIG. 16 show a variation of the invention having two secondary diameters. The coil 186 is preconditioned so that it has a larger secondary diameter (154) and a smaller secondary diameter (156). In this way, the larger secondary diameter (154) may be chosen to match that of the vascular site to be treated. The smaller secondary diameter (156) therefore ends up in the middle area of the targeted vascular region. The placement of the portion of the coil having a smaller secondary diameter away from the vessel wall enhances the propensity of the coil to occlude the site. The presence of the braided or woven covering 188 on the outside of the coil further augments the tendency of the coil-braid combination towards production of an embolus.

Figure 17:
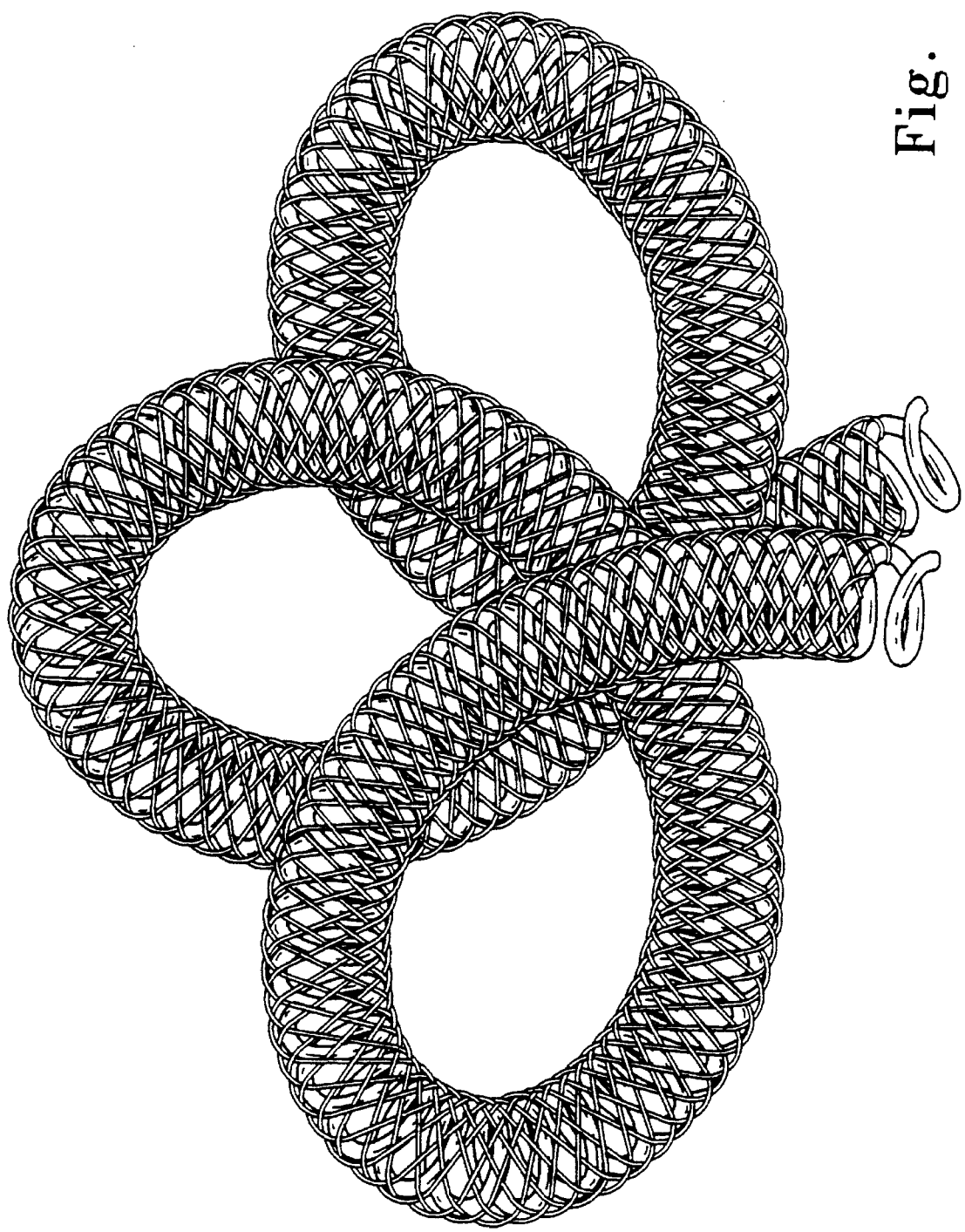

FIG. 17 show a variation of the invention shown in FIG. 14. In this instance the relaxed and braid 190 covered coil forms only a "cloverleaf". This is believed to be somewhat more controllable from a physical placement point of view and consequently is of great use to attending physicians. Again the presence of the braided covering enhances the coil assembly's facility to produce occluding material.

Figure 18:
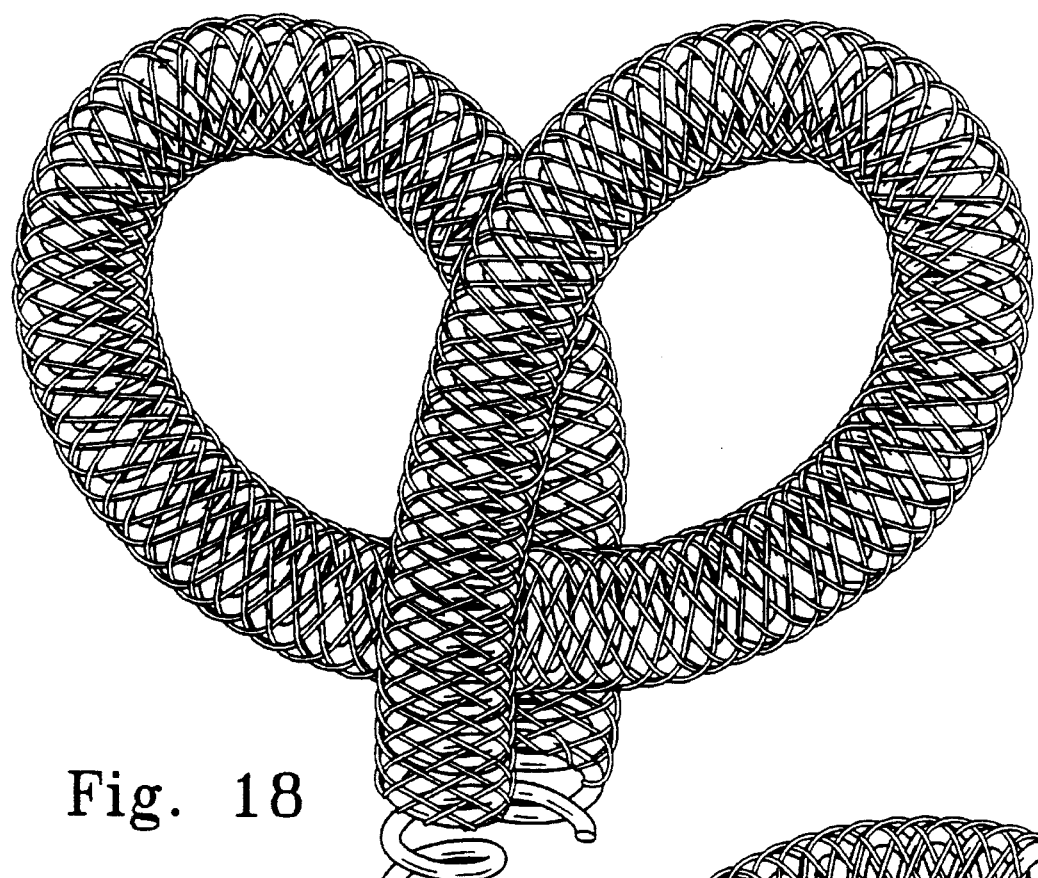
Figure 19:
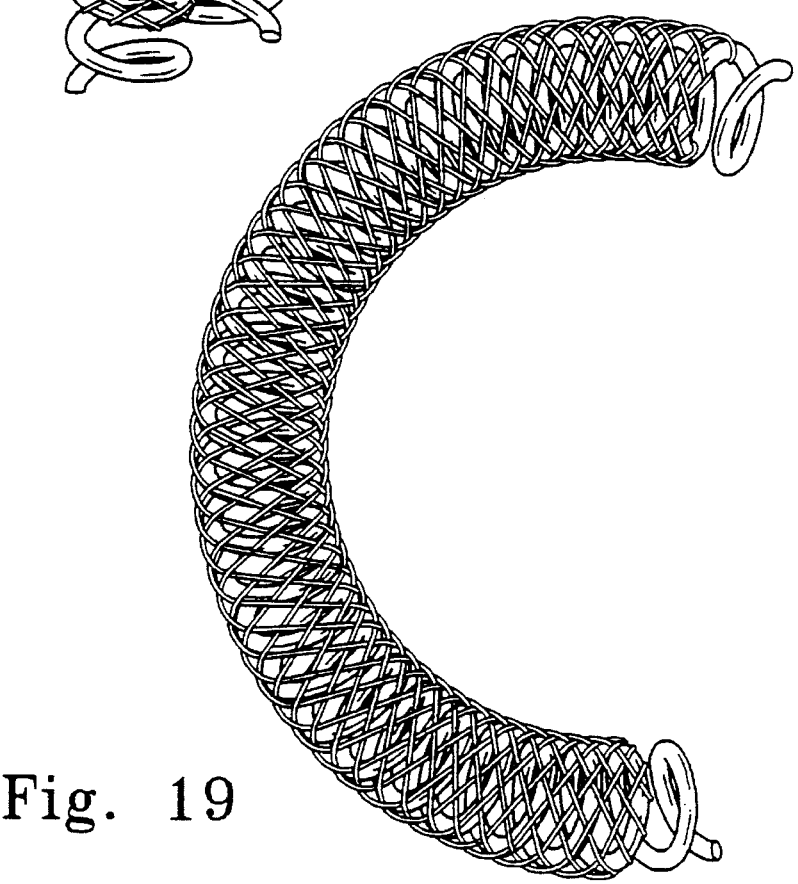

FIG. 18 shows a similar two-loop Coil (94) design and FIG. 19 shows the C-shaped design with braid (196) mentioned above. The FIG. 17 and 18 devices may be sized in such a fashion that they nest tightly within the vascular pocket or vessel which is to be occluded by the device.

Figure 20:
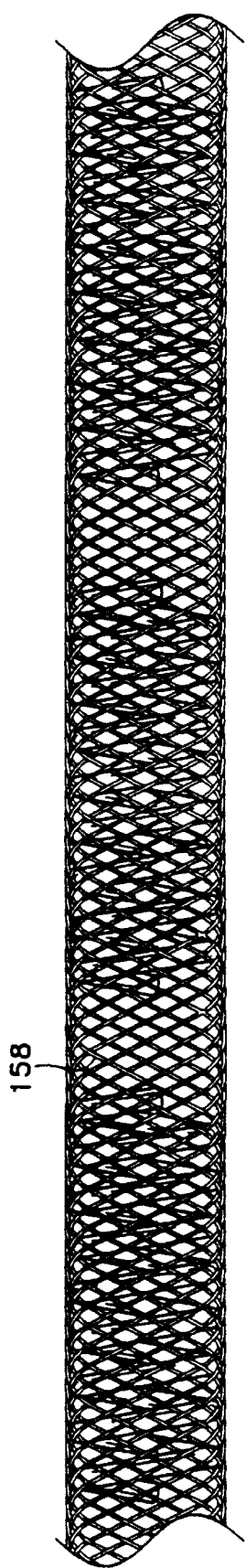

FIG. 20 shows a variation in which a single outer woven or braided covering 158 encloses a number of individual coils.

Figure 21:
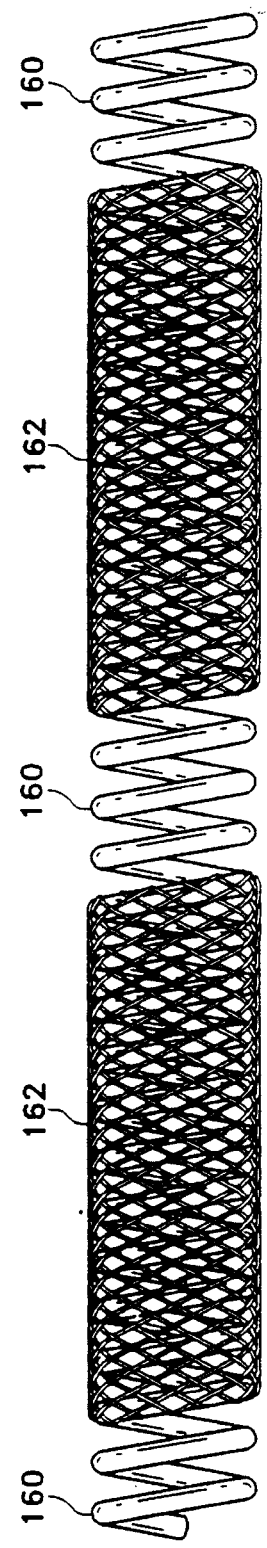

FIG. 21 shows another variation in which coils 160 are used to join a number of braided covers 150. Again, the FIG. 20 and 21 are variations of a type which allows a large number of coils and braids linked together to be placed upon a guide wire and injected from the catheter with relative ease. These configurations allow the occlusion device to be randomly jumbled at the site so to efficiently occlude the vascular opening.

Modification of the above-described variations of carrying out the invention that are obvious to those of skill in the fields of medical device design generally, and vasoocclusion devices specifically, are intended to be within the scope of the following claims.

We claim as our invention:

1. A vasoocclusive device adapted, sized, and configured for introduction into a vascular lumen consisting essentially of:
   a. a helical coil having a multiplicity of windings and having a first end and a second end, a passageway between the first end and second end, and
   b. at least one fibrous woven tubular member extending coaxially about at least a portion of the helical coil and adhering to the helical coil at least one location on the coil where the device is of a diameter which may be introduced through the lumen of a vascular catheter and of a diameter which is smaller than the diameter of the vascular lumen.

2. The device of claim 1 in which the helical coil is segmented.

3. The device of claim 2 in which the fibrous woven tubular member is braided.

4. The device of claim 3 in which the fibrous woven tubular member has an inside and an outside and wherein the device additionally comprises tassels extending beyond the outside of said tubular member.

5. The device of claim 1 in which the helical coil is continuous.

6. The device of claim 1 in which the fibrous at least one woven tubular member is braided.

7. The device of claim 6 in which the fibrous at least woven tubular member has an inside and an outside and wherein the device additionally comprises tassels extending beyond the outside of said tubular member.

8. The device of claim 6 where the helical coil assumes a random configuration when utilized.

9. The device of claim 6 when the helical coil assumes a cloverleaf configuration where relaxed.

10. The device at claim 6 where the helical coil assumes a regular coiled configuration where relaxed.

11. The device of claim 6 where the helical coil assumes a coiled shape having two secondary diameters where relaxed.

12. The device of claim 1 including multiple fibrous woven tubular members.

13. The device of claim 12 where the tubular members have a first end and a second end.

14. The device of claim 13 where the tubular member first ends are attached to the helical coil.

15. The device of claim 14 where the tubular member second ends are also attached to the helical coil.

16. The device of claim 15 where the tubular members are axially compressed on the axis between their first and second ends and bulge from the coil.

17. The device of claim 1 where the helical coil has a diameter of 0.008 to 0.018 inches.

* * * * *

UNITED STATES PATENT AND TRADEMARK OFFICE
CERTIFICATE OF CORRECTION

PATENT NO. : 5,522,822
DATED : June 4, 1996
INVENTOR(S) : PHELPS et al.

It is certified that error appears in the above-indentified patent and that said Letters Patent is hereby corrected as shown below:

column 1, line 29: change "Richart" to --Ritchart--.

column 2, line 29: delete "a".

column 3, line 22: change "Nitinol" to --nitinol-- (the first instance).

column 3, line 67: insert --(166)-- after "portion".

column 4, line 7: insert --(172)-- after "bulges".

column 4, line 7: insert --(164)--after "coil" (the second instance).

column 4, line 8: delete "172".

column 4, line 13: change "coil" to --coils--.

column 4, line 17: delete "176" after "diameter" (the second instance).

column 4, line 19: insert --(176)-- after "diameter".

column 4, line 35: change "show" to --shows--.

UNITED STATES PATENT AND TRADEMARK OFFICE
CERTIFICATE OF CORRECTION

PATENT NO. : 5,522,822

DATED : June 4, 1996

INVENTOR(S) : PHELPS et al.

It is certified that error appears in the above-indentified patent and that said Letters Patent is hereby corrected as shown below:

column 4, line 49: insert --(192)-- after "coil".

column 4, line 55: change "Coil (94)" to --coil (194)--.

column 4, line 55: insert --with braid (196) after "design".

column 4, line 56: change "C-shaped" to --c-shaped coil (198)--.

column 4, line 56: change "(196)" to --(200)--.

*Claim 6, column 6, line 3*: change "claim 1" to --claim 5--.

*Claim 7, column 6, line 5*: insert --one-- after "least".

Signed and Sealed this

Third Day of June, 1997

Attest:

BRUCE LEHMAN

Attesting Officer      *Commissioner of Patents and Trademarks*